(12) United States Patent
Kappel

(10) Patent No.: US 11,960,518 B2
(45) Date of Patent: Apr. 16, 2024

(54) SYSTEM AND METHOD FOR PROCESSING BIOLOGY-RELATED DATA, A SYSTEM AND METHOD FOR CONTROLLING A MICROSCOPE AND A MICROSCOPE

(71) Applicant: Leica Microsystems CMS GmbH, Wetzlar (DE)

(72) Inventor: Constantin Kappel, Schriesheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 194 days.

(21) Appl. No.: 17/596,289

(22) PCT Filed: Jun. 7, 2019

(86) PCT No.: PCT/EP2019/064967
§ 371 (c)(1),
(2) Date: Dec. 7, 2021

(87) PCT Pub. No.: WO2020/244775
PCT Pub. Date: Dec. 10, 2020

(65) Prior Publication Data
US 2022/0229862 A1  Jul. 21, 2022

(51) Int. Cl.
*G06F 16/00*   (2019.01)
*G06F 16/33*   (2019.01)
(Continued)

(52) U.S. Cl.
CPC ........ *G06F 16/3344* (2019.01); *G06F 16/583* (2019.01); *G06F 18/22* (2023.01);
(Continued)

(58) Field of Classification Search
None
See application file for complete search history.

(56) References Cited

U.S. PATENT DOCUMENTS

2003/0123737 A1*  7/2003  Mojsilovic ............ G06F 16/583
                                                        707/E17.02
2005/0123181 A1   6/2005  Freund et al.
(Continued)

FOREIGN PATENT DOCUMENTS

JP    2010529518 A    8/2010
JP    2014029732 A    2/2014
(Continued)

*Primary Examiner* — Thu Nguyet T Le
(74) *Attorney, Agent, or Firm* — 2SPL Patent Attorneys PartG mbB; Kieran O'Leary

(57) ABSTRACT

Embodiments relate to a system (100) comprising one or more processors (110) and one or more storage devices (120). The system (100) is configured to receive biology-related language-based search data (101) and generate a first high-dimensional representation of the biology-related language-based search data (101) by a trained language recognition ma-chine-learning algorithm executed by the one or more processors (110). The first high-dimensional representation comprises at least 3 entries each having a different value. Further, the system is configured to obtain a plurality of second high-dimensional representations (105) of a plurality of biology-related image-based input data sets or of a plurality of biology-related language-based input data sets and compare the first high-dimensional representation with each second high-dimensional representation of the plurality of second high-dimensional representations (105).

33 Claims, 6 Drawing Sheets

(51) Int. Cl.
*G06F 16/583* (2019.01)
*G06F 18/22* (2023.01)
*G06F 40/40* (2020.01)
*G06N 3/044* (2023.01)
*G06N 3/045* (2023.01)
*G06N 3/082* (2023.01)
*G16H 30/20* (2018.01)
*G16H 30/40* (2018.01)

(52) U.S. Cl.
CPC ............ *G06F 40/40* (2020.01); *G06N 3/044* (2023.01); *G06N 3/045* (2023.01); *G06N 3/082* (2013.01); *G16H 30/20* (2018.01); *G16H 30/40* (2018.01)

(56) References Cited

U.S. PATENT DOCUMENTS

| | | | |
|---|---|---|---|
| 2014/0214391 A1* | 7/2014 | Cope | G16B 35/10 703/11 |
| 2016/0246045 A1* | 8/2016 | Watanabe | G02B 21/0084 |
| 2018/0232451 A1 | 8/2018 | Lev-Tov et al. | |
| 2021/0049406 A1* | 2/2021 | Lu | G06F 16/583 |

FOREIGN PATENT DOCUMENTS

| | | |
|---|---|---|
| JP | 2018077806 A | 5/2018 |
| WO | 2018119200 A1 | 6/2018 |
| WO | 2018190792 A1 | 10/2018 |

* cited by examiner

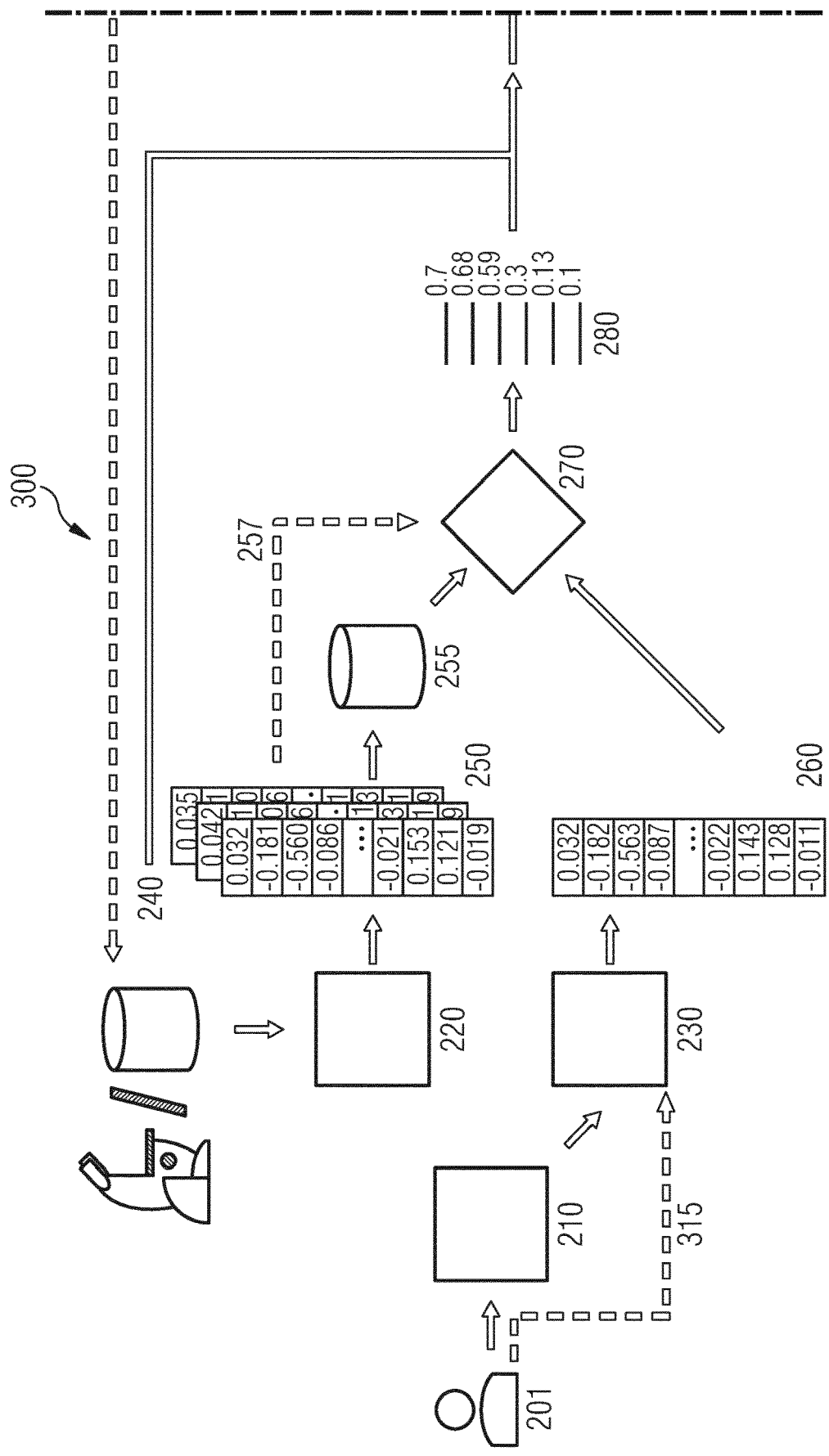

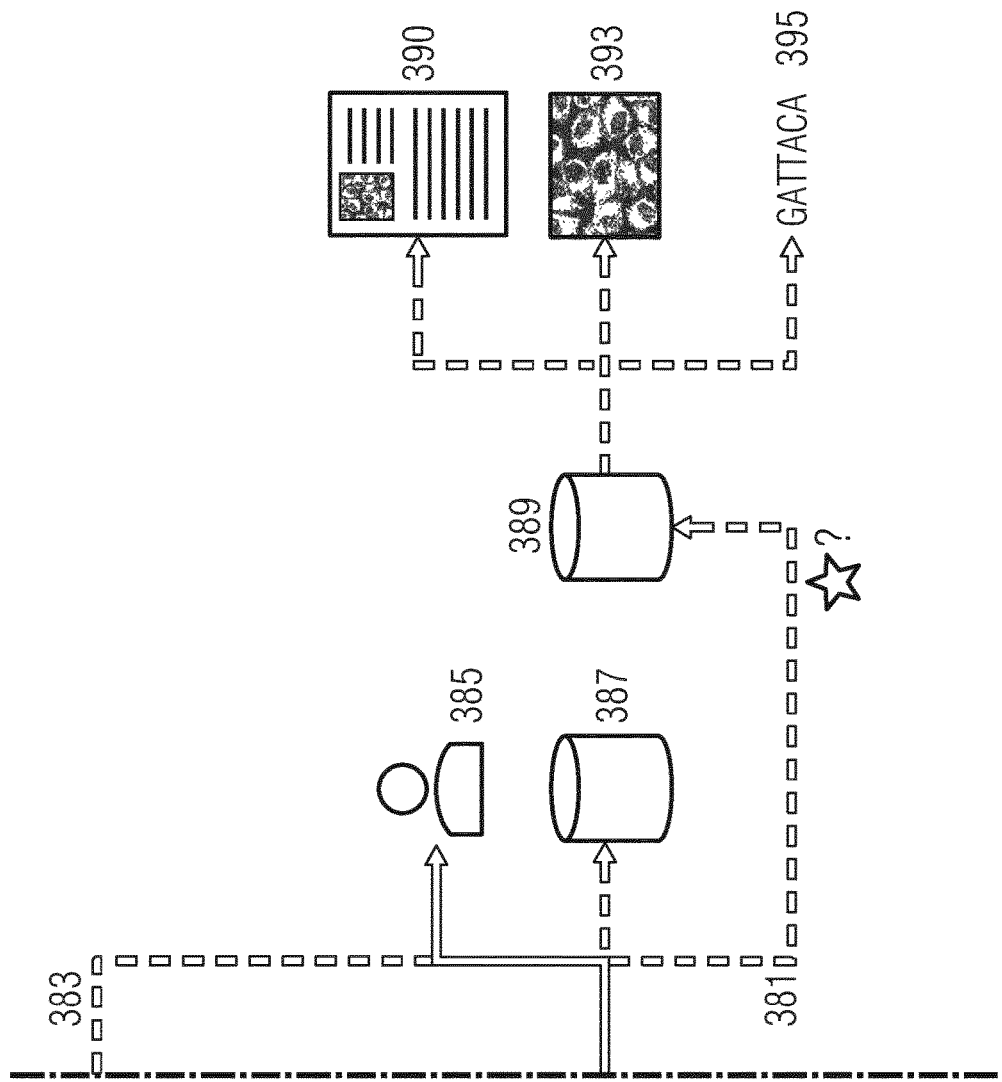

SYSTEM AND METHOD FOR PROCESSING BIOLOGY-RELATED DATA, A SYSTEM AND METHOD FOR CONTROLLING A MICROSCOPE AND A MICROSCOPE

TECHNICAL FIELD

Examples relate to the processing of biology-related data and/or the control of a microscope.

BACKGROUND

In many biological applications, a vast amount of data is generated. For example, images are taken from a huge amount of biological structures and stored in databases. It is very time-consuming and expensive to analyze the biological data manually.

SUMMARY

Hence, there is a need for an improved concept for processing biology-related data and/or the control of a microscope.

This need may be satisfied by the subject matter of the claims.

Some embodiments relate to a system comprising one or more processors coupled to one or more storage devices. The system is configured to receive biology-related language-based search data and configured to generate a first high-dimensional representation of the biology-related language-based search data by a trained language recognition machine-learning algorithm executed by the one or more processors. The first high-dimensional representation comprises at least 3 entries each having a different value. Further, the system is configured to obtain a plurality of second high-dimensional representations of a plurality of biology-related image-based input data sets or of a plurality of biology-related language-based input data sets. Additionally, the system is configured to compare the first high-dimensional representation with each second high-dimensional representation of the plurality of second high-dimensional representations.

By using a language recognition machine-learning algorithm a textual biological search term can be mapped to a high-dimensional representation. By allowing the high-dimensional representation to have entries with various different values (in contrast to one hot encoded representations), semantically similar biological search terms can be mapped to similar high-dimensional representations. By obtaining high-dimensional representations of a plurality of biology-related image-based input data sets or of a plurality of biology-related language-based input data sets, high-dimensional representations can be found equal or similar to the high-dimensional representation of the search term. In this way, it may be enabled to find images or text corresponding to the search term. In this way, the trained language recognition machine-learning algorithm may enable a search for biology-related images among a plurality of biological images (e.g. database of biological images) or a search for biology-related texts among a plurality of biology related texts (e.g. scientific paper collection or library) based on a language-based search input. A search within an already existing database or images generated by a running experiment (e.g. images taken by a microscope of one or more biological specimens) may be enabled, even if the images were not labeled or tagged before.

Some embodiments relate to a system comprises one or more processors and one or more storage devices. The system is configured to receive language-based search data and configured to generate a first high-dimensional representation of the language-based search data by a trained language recognition machine-learning algorithm executed by the one or more processors. The first high-dimensional representation comprises at least 3 entries each having a different value. Further, the system is configured to obtain a plurality of second high-dimensional representations of a plurality of image-based input data sets and configured to select a second high-dimensional representation from the plurality of second high-dimensional representations based on a comparison of the first high-dimensional representation with each second high-dimensional representation of the plurality of second high-dimensional representations. Additionally, the system is configured to provide a control signal for controlling an operation of a microscope based on the selected second high-dimensional representation.

By using a language recognition machine-learning algorithm a textual search term can be mapped to a high-dimensional representation. By allowing the high-dimensional representation to have entries with various different values (in contrast to one hot encoded representations), semantically similar search terms can be mapped to similar high-dimensional representations. By obtaining high-dimensional representations of a plurality of image-based input data sets, high-dimensional representations can be found equal or similar to the high-dimensional representation of the search term. In this way, it may be enabled to find images corresponding to the search term. With this information, a microscope can be driven to the respective locations, the images were taken, in order to enable taking further images (e.g. with higher magnification, different light or filter) of the locations of interest. In this way, a specimen (e.g. biological specimen or integrated circuit) may be imaged at low magnification first to find locations corresponding to the search term and afterwards the locations of interest may be analyzed in more detail.

SHORT DESCRIPTION OF THE FIGURES

Some examples of apparatuses and/or methods will be described in the following by way of example only, and with reference to the accompanying figures, in which FIG. 1 is a schematic illustration of a system for processing biology-related data;

FIG. 3 is a schematic illustration of another system for processing biology-related data;

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Same or like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B, if not explicitly or implicitly defined otherwise. An alternative wording for the same combinations is "at least one of A and B" or "A and/or B". The same applies, mutatis mutandis, for combinations of more than two Elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Figure 1:
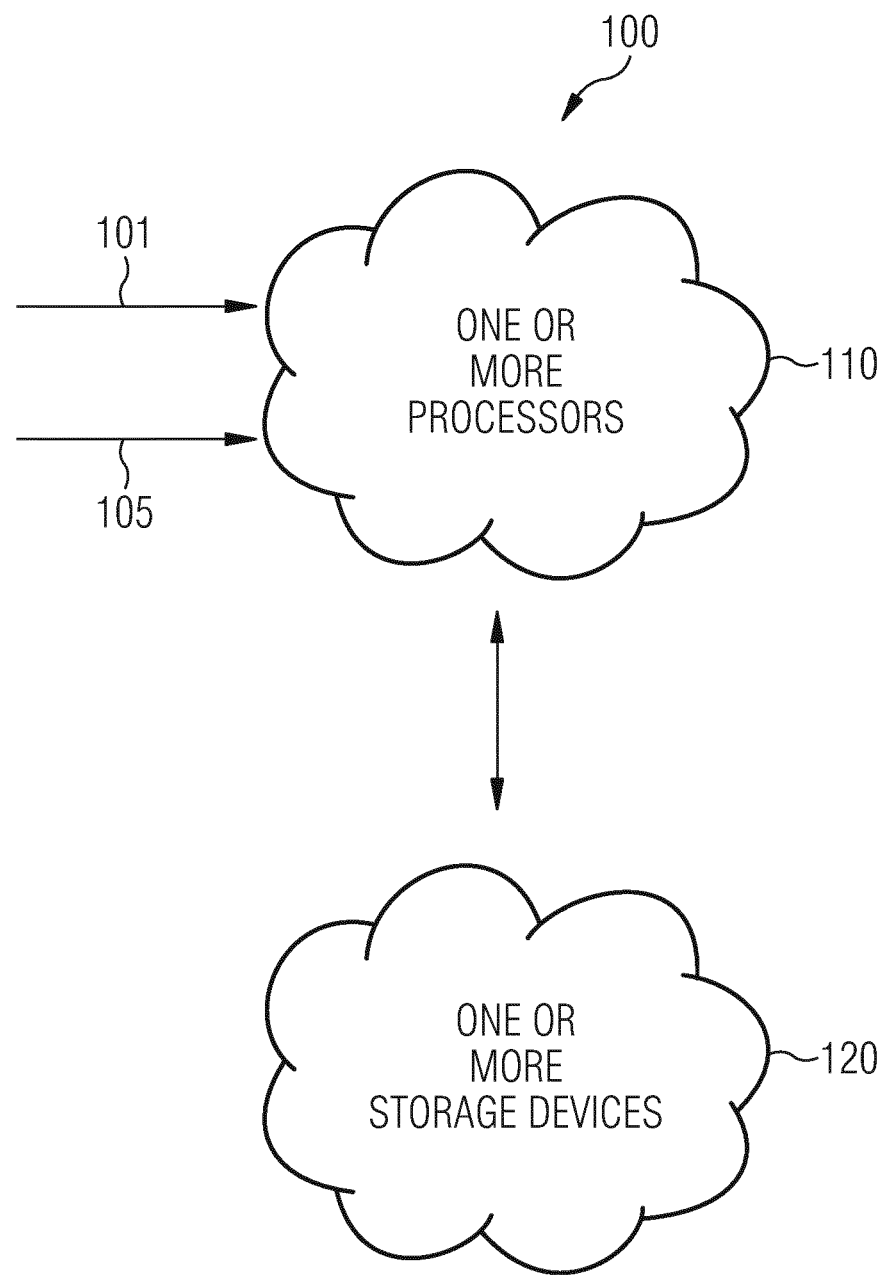

FIG. 1 shows a schematic illustration of a system 100 for processing biology-related data according to an embodiment. The system 100 comprises one or more processors 110 coupled to one or more storage devices 120. The system 100 is configured to receive (first) biology-related language-based search data 101 and configured to generate a first high-dimensional representation of the (first) biology-related language-based search data 101 by a trained language recognition machine-learning algorithm executed by the one or more processors 110. The first high-dimensional representation comprises at least 3 entries each having a different value (or at least 20 entries, at least 50 entries or at least 100 entries having values different from each other). Further, the system 100 is configured to obtain a plurality of second high-dimensional representations 105 of a plurality of biology-related image-based input data sets or of a plurality of biology-related language-based input data sets. Additionally, the system 100 is configured to compare the first high-dimensional representation with each second high-dimensional representation 105 of the plurality of second high-dimensional representations by the one or more processors 110.

The biology-related language-based search data 101 may be a textual input being related to a biological structure, a biological function, a biological behavior or a biological activity. For example, the biology-related language-based search data 101 may be a nucleotide sequence, a protein sequence, a description of a biological molecule or biological structure, a description of a behavior of a biological molecule or biological structure, and/or a description of a biological function or a biological activity. The textual input may be natural language, which is descriptive of the biological molecule (e.g. polysaccharide, poly/oligonucleotide, protein or lipid) or its behavior in the context of the experiment or data set. For example, the biology-related language-based search data 101 may be a nucleotide sequence, a protein sequence or a coarse-grained search term of a group of biological terms.

A group of biological terms may comprise a plurality of coarse-grained search terms (or alternatively called molecular biological subject heading terms) belonging to the same biological topic. A group of biological terms may be catalytic activity (e.g. as some sort of reaction equation using words for educts and products), pathway (e.g. which pathway is involved, for example, glycolysis), sites and/or regions (e.g. binding site, active site, nucleotide binding site), GO gene ontology (e.g. molecular function, for example, nicotinamide adenine dinucleotide NAD binding, microtubule binding), GO biological function (e.g. apoptosis, gluconeogenesis), enzyme and/or pathway databases (e.g. unique identifiers for sic function, for example, in BRENDA/EC number or UniPathways), subcellular localization (e.g. cytosol, nucleus, cytoskeleton), family and/or domains (e.g. binding sites, motifs, e.g. for posttranslational modification), open-reading frames, single-nucleotide polymorphisms, restriction sites (e.g. oligonucleotides recognized by a restriction enzyme) and/or biosynthesis pathway (e.g. biosynthesis of lipids, polysaccharides, nucleotides or proteins). For example, the group of biological terms may be the group of subcellular localizations and the coarse-grained search terms may be cytosol, nucleus and cytoskeleton. In this example, images with cytosol, nucleus or cytoskeleton may be searched for, if cytosol, nucleus or cytoskeleton is used as biology-related language-based search data 101.

The biology-related language-based search data 101 may comprise a length of less than 50 characters (or less than 30 characters or less than 20 characters), if a coarse-grained search term is used as biology-related language-based search data 101, and/or more than 20 characters (or more than 40 characters, more than 60 characters or more than 80 characters), if a nucleotide sequence or a protein sequence is used as biology-related language-based search data 101. For example, nucleotide sequences (DNA/RNA) are often about three times longer than polypeptide sequences (e.g. peptide, protein), since three base pairs are coded for an amino acid. For example, the biology-related language-based search data 101 may comprise a length of more than 20 characters, if the biology-related language-based search data 101 is a protein sequence or an amino acid. The biology-related language-based search data 101 may comprise a length of more than 60 characters, if the biology-related language-based search data 101 is a nucleotide sequence or descriptive text in natural language. For example, the biology-related language-based search data 101 may comprise at least one non-numerical character (e.g. an alphabetical character). The biology-related language-based search data 101 may also be called query text, query, input text or user input. The biology-related language-based search data 101 may be input by a user through an input interface (e.g. keyboard) of the system 100.

A high-dimensional representation (e.g. first and second high-dimensional representation) may be a hidden representation, a latent vector, an embedding, a sematic embedding and/or a token embedding and/or may be also called hidden representation, a latent vector, an embedding, a semantic embedding and/or a token embedding.

The first high-dimensional representation and/or the second high-dimensional representations may be numerical representations (e.g. comprising numerical values only). In contrast, the biology-related language-based search data 101 may comprise alphabetic characters or other non-numeric characters only or a mixture of alphabetic characters, other non-numeric characters and/or numerical characters. The first high-dimensional representation and/or the second high-dimensional representations may comprise more than 100 dimensions (or more than 300 dimensions or more than 500 dimensions) and/or less than 10000 dimensions (or less than 3000 dimensions or less than 1000 dimensions). Each entry of a high-dimensional representation may be a dimension of the high-dimensional representation (e.g. a high-dimensional representation with 100 dimensions comprises 100 entries). For example, using high dimensional representations with more than 300 dimensions and less than 1000 dimensions may enable a suitable representation for biology-related data with semantic correlation. The first high-dimensional representation may be a first vector and each second high-dimensional representation may be a respective second vector. If a vector representation is used for the entries of the first high-dimensional representation and the entries of a second high-dimensional representation, an efficient comparison and/or other calculations (e.g. normalization) may be implemented, although other representations (e.g. as a matrix) may be possible as well. For example, the first high-dimensional representation and/or the second high-dimensional representations may be normalized vectors. The first high-dimensional representation and the second high-dimensional representations may be normalized to the same value (e.g. 1). For example, the last layer of the trained language recognition machine-learning algorithm may represent a non-linear operation, which may perform the normalization in addition. For example, if the trained language recognition machine-learning algorithm was trained with the cross entropy loss function, a so-called SoftMax operation may be implemented:

$$\text{softmax} = \frac{e^{\hat{y}_i}}{\sum_{i}^{K} e^{\hat{y}_i}}$$

with $y_i$ being a prediction of the model corresponding to an input value and K being the number of all input values. In this way, the trained language recognition machine-learning algorithm may output normalized high-dimensional representations. The second high-dimensional representations may be generated by a trained visual recognition machine-learning algorithm, which may have been trained by a loss function, which causes the trained visual recognition machine-learning algorithm to output normalized high-dimensional representations. However, other approaches for the normalization of the first high-dimensional representation and the second high-dimensional representations may be applicable as well.

For example, the first high-dimensional representation and/or the second high-dimensional representations may comprise various entries (at least three) with values unequal 0 in contrast to one hot encoded representations. Corresponding to the first high-dimensional representation, each second high-dimensional representation of the plurality of second high-dimensional representations may comprise at least 3 entries each having a different value (or at least 20 entries, at least 50 entries or at least 100 entries having values different from each other). By using high-dimensional representation, which can have various entries with values unequal 0, information on a semantic relationship between the high-dimensional representations can be reproduced. For example, more than 50% (or more than 70% or more than 90%) of values of the entries of the first high-dimensional representation and/or more than 50% (or more than 70% or more than 90%) of values of the entries of the second high-dimensional representations may be unequal 0. Sometimes one hot encoded representations have also more than one entry unequal 0, but there is only one entry with high value and all other entries have values at noise level (e.g. lower than 10% of the one high value). In contrast, the values of more than 5 entries (or more than 20 entries or more than 50 entries) of the first high-dimensional representation may be larger than 10% (or larger than 20% or larger than 30%) of a largest absolute value of the entries of the first high-dimensional representation, for example. Further, the values of more than 5 entries (or more than 20 entries or more than 50 entries) of each second high-dimensional representation of the plurality of second high-dimensional representations may be larger than 10% (or larger than 20% or larger than 30%) of a respective largest absolute value of the entries of the second high-dimensional representations. For example, the values of more than 5 entries (or more than 20 entries or more than 50 entries) of one second high-dimensional representation of the plurality of second high-dimensional representations may be larger than 10% (or larger than 20% or larger than 30%) of a largest absolute value of the entries of the one second high-dimensional representation. For example, each entry of the first high-dimensional representation and/or the second high-dimensional representations may comprise a value between −1 and 1.

The first high-dimensional representation may be determined by applying at least a part (e.g. encoder) of the trained language recognition machine-learning algorithm with a trained set of parameters to the biology-related language-based search data 101. For example, generating the first high-dimensional representations by the trained language recognition machine-learning algorithm may mean that the first high-dimensional representation is generated by an encoder of the trained language recognition machine-learning algorithm. The trained set of parameters of the trained language recognition machine-learning algorithm may be obtained during training of the language recognition machine-learning algorithm as described below.

The values of one or more entries of the first high-dimensional representation and/or the values of one or more entries of the second high-dimensional representations may be proportional to a likelihood of a presence of a specific biological function or a specific biological activity. By using a mapping that generates high-dimensional representations preserving the semantical similarities of the input data sets, semantically similar high-dimensional representations may have a closer distance to each other than semantically less similar high-dimensional representations. Further, if two high-dimensional representations represent input data sets with same or similar specific biological function or specific biological activity one or more entries of these two high-dimensional representations may have same or similar values. Due to the preservation of the semantic, one or more entries of the high-dimensional representations may be an indication of an occurrence or presence of a specific biological function or a specific biological activity. For example, the higher a value of one or more entries of the high-dimensional representation, the higher the likelihood of a presence of a biological function or a biological activity correlated with these one or more entries may be.

The trained language recognition machine-learning algorithm may also be called textual model, text model or language model. The language recognition machine-learning algorithm may be or may comprise a trained language recognition neural network. The trained language recognition neural network may comprise more than 30 layers (or more than 50 layers or more than 80 layers) and/or less than 500 layers (or less than 300 layers or less than 200 layers). The trained language recognition neural network may be a recurrent neural network, for example, a long short-term memory network. Using a recurrent neural network, for example a long short-term memory network, may provide a language recognition machine-learning algorithm with high accuracy for biology-related language-based data. However, also other language recognition algorithms may be applicable. For example, the trained language recognition machine-learning algorithm may be an algorithm able to handle input data of variable length (e.g. Transformer-XL algorithm). For example, a length of first biology-related language-based search data differs from a length of second biology-related language-based search data. Protein sequences, for example, typically are tens to hundreds of amino acids long (with one amino acid represented as one letter in the protein sequence). The "semantics", e.g. biological function of substrings from the sequence (called polypeptides, motifs or domains in biology) may vary in length. Thus, using an architecture which is capable of receiving input of variable length may be used.

The plurality of second high-dimensional representations 105 of the plurality of biology-related image-based input data sets or of the plurality of biology-related language-based input data sets may be obtained by receiving the second high-dimensional representations 105 from a database (e.g. stored by the one or more storage devices) or by generating the plurality of second high-dimensional representations 105 based on the plurality of biology-related image-based input data sets or the plurality of biology-related language-based input data sets. For example, the system 100 may be configured to obtain the second high-dimensional representations by generating the second high-dimensional representations of the plurality of second high-dimensional representations by a trained visual recognition machine-learning algorithm executed by the one or more processors, if the plurality of second high-dimensional representations is based on a plurality of biology-related image-based input data sets. For example, the trained visual model may be able to represent an image in the semantic embedding space (e.g. as second high dimensional representation). Alternatively, the system 100 may be configured to obtain the second high-dimensional representations by generating the second high-dimensional representations of the plurality of second high-dimensional representations by a trained language recognition machine-learning algorithm executed by the one or more processors, if the plurality of second high-dimensional representations is based on a plurality of biology-related language-based input data sets.

Each biology-related image-based input data set of the plurality of biology-related image-based input data sets may be image data (e.g. pixel data of an image) of an image of a biological structure comprising a nucleotide or a nucleotide sequence, a biological structure comprising a protein or a protein sequence, a biological molecule, a biological tissue, a biological structure with a specific behavior, and/or a biological structure with a specific biological function or a specific biological activity. The biological structure may be a molecule, a viroid or virus, artificial or natural membrane enclosed vesicles, a subcellular structure (like a cell organelle) a cell, a spheroid, an organoid, a three-dimensional cell culture, a biological tissue, an organ slice or part of an organ in vivo or in vitro. For example, the image of the biological structure may be an image of the location of a protein within a cell or tissue or an image of a cell or tissue with endogenous nucleotides (e.g. DNA) to which labeled nucleotide probes bind (e.g. in situ hybridization). The image data may comprise a pixel value for each pixel of an image for each color dimension of the image (e.g. three color dimensions for RGB representation). For example, depending on the imaging modality other channels may apply related to excitation or emission wavelength, fluorescence lifetime, light polarization, stage position in three spatial dimensions, different imaging angles. The biology-related image-based input data set may be an XY pixel map, volumetric data (XYZ), time series data (XY+T) or combinations thereof (XYZT). Moreover, additional dimensions depending on the kind of image source may be included such as channel (e.g. spectral emission bands), excitation wavelength, stage position, logical position as in a multi-well plate or multi-positioning experiment and/or mirror and/or objective position as in lightsheet imaging. For example, the user may input or a database may provide an image as a pixel map or pictures of higher dimensions. The trained visual recognition machine-learning algorithm may convert this image into semantic embeddings (e.g. second high-dimensional representation). The plurality of biology-related image-based input data sets may be received from the one or more storage devices or a database stored by a storage device.

Similar to the biology-related language-based search data 101, each biology-related language-based input data set of the plurality of biology-related language-based input data sets may be a textual input being related to a biological structure, a biological function, a biological behavior or a biological activity. For example, each biology-related language-based input data set of the plurality of biology-related language-based input data sets may be a nucleotide sequence, a protein sequence, a description of a biological molecule or biological structure, a description of a behavior of a biological molecule or biological structure, and/or a description of a biological function or a biological activity. The textual input may be natural language, which is descriptive of the biological molecule (e.g. polysaccharide, poly/oligo-nucleotide, protein or lipid) or its behavior in the context of the experiment or data set. For example, each biology-related language-based input data set of the plurality of biology-related language-based input data sets may be a nucleotide sequence, a protein sequence or a coarse-grained search term of a group of biological terms.

The trained visual recognition machine-learning algorithm may also be called image recognition model or visual model. The trained visual recognition machine-learning algorithm may be or may comprise a trained visual recognition neural network. The trained visual recognition neural network may comprise more than 20 layers (or more than 40 layers or more than 80 layers) and/or less than 400 layers (or less than 200 layers or less than 150 layers). The trained visual recognition neural network may be a convolutional neural network or a capsule network. Using a convolutional neural network or a capsule network may provide a trained visual recognition machine-learning algorithm with high accuracy for biology-related image-based data. However, also other visual recognition algorithms may be applicable. For example, the trained visual recognition neural network may comprise a plurality of convolution layers and a plurality of pooling layers. However, pooling layers may be avoided, if a capsule network is used and/or stride=2 is used instead of stride=1 for the convolution, for example. The trained visual recognition neural network may use a rectified linear unit activation function. Using a rectified linear unit activation function may provide a trained visual recognition machine-learning algorithm with high accuracy for biology-related image-based input data, although other activation functions (e.g. a hard tanh activation function, a sigmoid activation function or a tanh activation function) may be applicable as well. For example, the trained visual recognition neural network may comprise a convolutional neural network and/or may be a ResNet or a DenseNet of a depth depending on the size of the input images.

The one or more processors 110 may be configured to compare the first high-dimensional representation with each second high-dimensional representation of the plurality of second high-dimensional representations. The first high-dimensional representation may be compared to a second high-dimensional representation by calculating a distance between the first high-dimensional representation and the second high-dimensional representation. The distance (e.g. Euclidean distance or earth mover's distance) between the first high-dimensional representation and the second high-dimensional representation may be calculated with low effort, if the first high-dimensional representation and the second high-dimensional representation are represented by vectors (e.g. normalized vectors). The calculation of the distance may be repeated for every second high-dimensional representation of the plurality of second high-dimensional representations. For example, the comparison of the first high-dimensional representation with each second high-dimensional representation of the plurality of second high-dimensional representations is based on an Euclidean distance function or an earth mover's distance function. Based on the calculated distances, the system 100 may select one or more second high-dimensional representations based on a selection criterion (e.g. the one or more second high-dimensional representations with closest distance or within a distance threshold). For example, the system 100 may be configured to select a second high-dimensional representation of the plurality of second high-dimensional representations closest to the first high-dimensional representation based on the comparison. The system 100 may output or store the one or more second high-dimensional representations fulfilling the selection criterion, the one or more biology-related image-based input data sets of the plurality of biology-related image-based input data sets, which correspond to the one or more second high-dimensional representations, and/or the one or more biology-related language-based input data sets of the plurality of biology-related language-based input data sets, which correspond to the one or more second high-dimensional representation. For example, the system 100 may output and/or store the closest second high-dimensional representation, the biology-related image-based input data set of the plurality of biology-related image-based input data sets, which corresponds to the closest second high-dimensional representation, and/or the biology-related language-based input data set of the plurality of biology-related language-based input data sets, which corresponds to the closest second high-dimensional representation.

Due to the usage of high dimensional representations with several entries unequal 0, a combination of two or more high dimensional representations may be possible in order to search for a logical combination of two or more search terms. For example, the user may input two or more search terms and one or more logical operators (e.g. AND-operator or NOT-operator) and the corresponding generated first high dimensional representations may be combined based on the logical operator. For example, the system may be configured to receive second biology-related language-based search data and information on a logical operator. Further, the system 100 may generate a first high-dimensional representation of the second biology-related language-based search data by the trained language recognition machine-learning algorithm executed by the one or more processors. Additionally, the system 100 may determine a combined high-dimensional representation based on a combination of the first high-dimensional representation of the first biology-related language-based search data and the first high-dimensional representation of the second biology-related language-based search data according to the logical operator. The combined high-dimensional representation may be a normalized high-dimensional representation (e.g. a normalized vector).

Further, the system 100 may compare the combined high-dimensional representation to each second high-dimensional representation of the plurality of second high-dimensional representations. Based on the comparison of the combined high-dimensional representation with each second high-dimensional representation of the plurality of second high-dimensional representations, one or more second high representations may be selected based on a selection criterion (e.g. the one or more second high-dimensional representations with closest distance or within a distance threshold).

The system 100 may output or store the one or more second high-dimensional representations fulfilling the selection criterion, the one or more biology-related image-based input data sets of the plurality of biology-related image-based input data sets, which correspond to the one or more second high-dimensional representations, and/or the one or more biology-related language-based input data sets of the plurality of biology-related language-based input data sets, which correspond to the one or more second high-dimensional representation. The selected one or more biology-related image-based input data sets (e.g. biological images) or the selected one or more biology-related language-based input data sets (e.g. biological text) may show or describe biological structures comprising the logical combination of search terms as represented by the first biology-related language-based search data, the second biology-related language-based search data and the information on the logical operator. In this way, a search for a logical combination of two or more search terms may be enabled. The logical operator may an AND-operator, an OR-operator or a NOT-operator. The NOT-operator may suppress undesired hits. The NOT-operation may be determined by a search for the negated search term. For example, the embedding (e.g. first high-dimensional representation) of the negated search term may be generated and inverted. Then the k embeddings closest to the embedding of the negated search term may be determined among the plurality of embeddings associated with the images (the plurality of second high-dimensional representations) and removed from the plurality of embeddings. Optionally, the mean (e.g. medoid or arithmetic mean) of the remaining plurality of embeddings may be determined. This newly computed second high-dimensional representation may serve for a new query in the embedding space to obtain more precise hits. The OR-operation may be implemented by determining the closest or k closest elements (second high-dimensional representation) for each search term with k being an integer number between 2 and N. For example, all OR-linked search terms may be searched in a loop and the closest or the k closest hits may be output. Further, a combination of several of the logical operators may be possible by parsing the expressions and working on the searches one after the other or from inside out.

For example, the logical operator is an AND-operator and the combined high-dimensional representation is determined by adding and/or averaging the first high-dimensional representation of the first biology-related language-based search data and the first high-dimensional representation of the second biology-related language-based search data. For example, the arithmetic mean of the first high-dimensional representation of the first biology-related language-based search data and the first high-dimensional representation of the second biology-related language-based search data may be determined. For example, the arithmetic mean may be determined by:

$$\frac{1}{N}\sum_{i}^{N} \hat{y}_i$$

with yi being a first high-dimensional representation and N being the number of vectors to be averaged (e.g. number of logical combined search terms). The determination of the arithmetic mean may result in a normalized high-dimensional representation. Alternatively, the geometric mean, the harmonic mean, the quadratic mean or the medoid may be used. The medoid may be used to avoid large errors for distributions with a hole (e.g. enclosed area with no data points). The medoid may find the element, which is closest to the mean. The medoid m may be defined as:

$$m = \mathrm{argmin}_{y_i \in Y} \sum_{i=1}^{N} d(\hat{y}, y_i)$$

with Y being the whole embeddings (plurality of second high-dimensional representations), yi being one of the second high-dimensional representations, ŷ being the embedding corresponding to the search term (first high-dimensional representation) and d being a distance metric (e.g. Euclidean distance or L2-norm). For example, the element of Y being closest to the mean may be found and afterwards the k elements being closest to the medoid may be determined (e.g. by a quicksort algorithm).

As mentioned above, the biology-related language-based search data 101 may be of various types (e.g. a nucleotide sequence, a protein sequence or a coarse-grained search term of a group of biological terms). A single language recognition machine-learning algorithm may be trained to handle one type of input only. Therefore, the system 100 may be configured to select the trained language recognition machine-learning algorithm from a plurality of trained language recognition machine-learning algorithms based on the biology-related language-based search data 101. For example, a plurality of trained language recognition machine-learning algorithms may be stored by the one or more storage devices 120 and the system 100 may select one of the trained language recognition machine-learning algorithms depending on the type of input received as biology-related language-based search data 101. For example, the trained language recognition machine-learning algorithm may be selected from a plurality of trained language recognition machine-learning algorithms by a classification algorithm (e.g. language recognition machine-learning algorithm) configured to classify the biology-related language-based search data 101.

The system 100 may be implemented in a microscope, may be connected to a microscope or may comprise a microscope. The microscope may be configured to obtain the plurality of biology-related image-based input data sets by taking images of one or more biological specimens. The plurality of biology-related image-based input data sets may be stored by the one or more storage devices 120 and/or may be provided for the generation of the plurality of second high-dimensional representations.

More details and aspects of the system 100 are mentioned in conjunction with the proposed concept and/or the one or more examples described above or below (e.g. FIGS. 2-7). The system 100 may comprise one or more additional optional features corresponding to one or more aspects of the proposed concept and/or of one or more examples described above or below.

Figure 2:
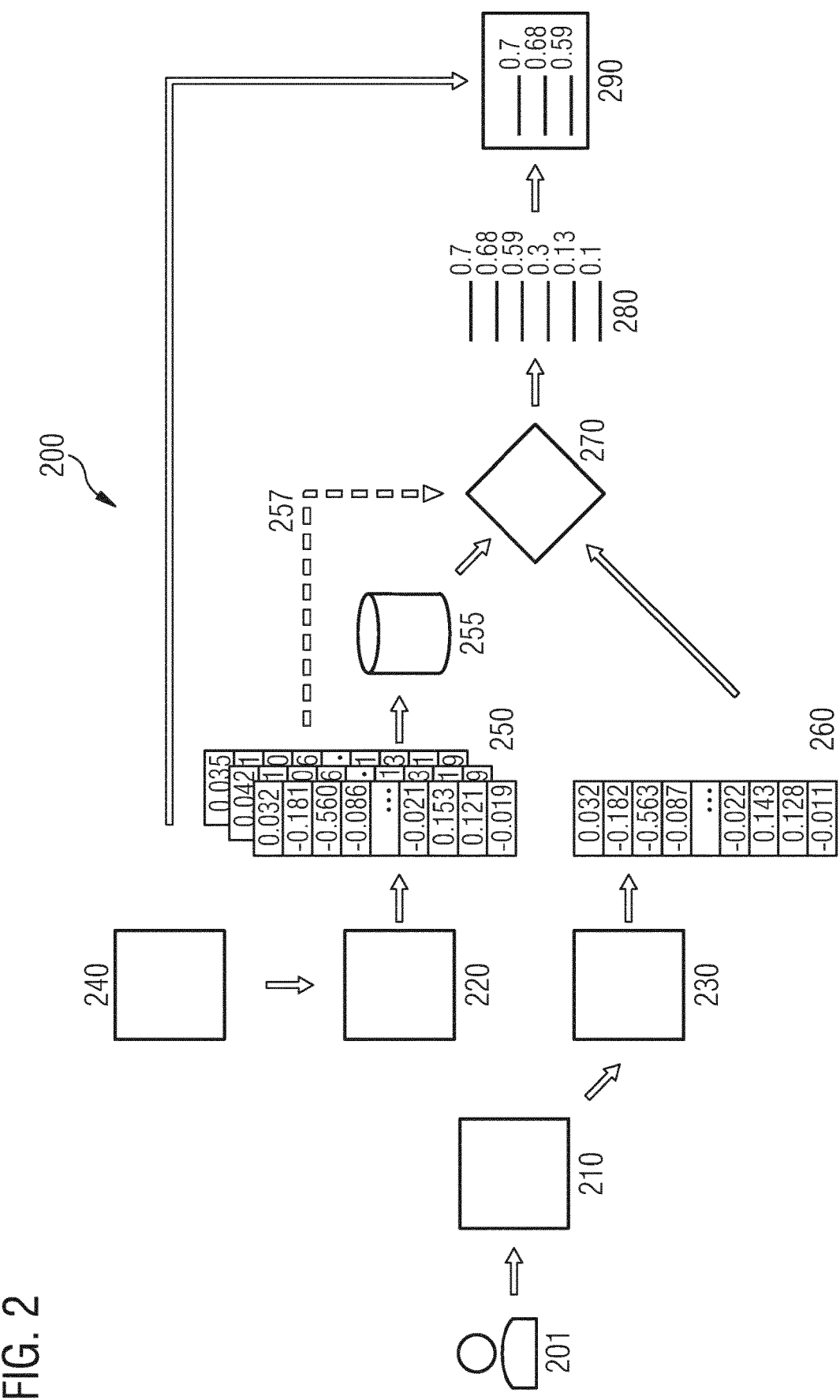
FIG. 2 is a schematic illustration of another system for processing biology-related data.

FIG. 2 shows a schematic illustration of a system 200 for processing biology-related data according to an embodiment. A user may start a query using text 201 (e.g. biology-related language-based search data) as in a protein sequence, nucleotide sequence or natural language. For example, the system 200 comprises a visual model 220 (e.g. CNN), which was trained on the semantic embeddings of a textual model, which was trained on a large body of protein sequences (e.g. protein sequence database), nucleotide sequences (e.g. nucleotide sequence database), scientific publications (e.g. database of biology-related publications) or other texts describing the role and/or biological function of the object of interest, such as blog posts, home pages of research groups, online articles, discussion forums or social media posts. For example, the visual model 220 has learned to predict these semantic embeddings during training as described below, but other ways of training the model may be possible. The user input 201 (e.g. query text) may be first classified by a text model 210 into the respective class (e.g. protein sequence, nucleotide sequence or natural language) and the system 200 may find the correct second textual model 230 for this class from a repository of such models containing one or more textual models necessary to process the classes of input text. The query text 201 is then transformed into its respective embedding 260 (first high-dimensional representation) using a forward pass through the respective pretrained language model 230 (trained language recognition machine-learning algorithm). The image data in the database 240 (e.g. stored by the one or more storage devices) or as part of a running experiment in a microscope may be transformed into their respective embeddings 250 (plurality of second high-dimensional representations) via a forward pass through a pretrained visual model 220 (trained visual recognition machine-learning algorithm). For example, for performance reasons this part could be done prior to the user query and stored in a suitable database 255 (e.g. stored by the one or more storage devices), or, for example, along with the image data. The database 240 and the database 255 may be identical or the same, but they could be different databases as well. However, for single or small numbers of images as in a running experiment the forward pass of the images can be done on-the-fly, thus bypassing 257 the intermediate storage 255 of the visual embeddings 250. For example, the image repository 240 can represent a public or private database or it can represent the storage medium of a microscope during a running experiment. The two kinds of generated embeddings, one embedding for the query text 260 and the embeddings for the images 250, can be compared 270 in embedding space (e.g. their relative distances can be computed). Different distance metrics can be used for this comparison, such as Euclidean distance or Earth mover's distance. Other distance metrics may be used as well (e.g. distance metrics used in clustering). For example, the closest embeddings 280 may be determined and the respective images 290 may be looked up in the repository 240 and returned to the user. The number of images to return may be pre-determined by the user or computed according to a distance threshold or other criterion. For example, the search for the one or more closest embeddings may provide the k closest elements out of the plurality of embeddings 250 (plurality of second high-dimensional representations) with k being an integer number. For example, the Euclidian distance (L2 norm) between the embedding of the search query and all elements of the plurality of embeddings 250 may be determined. The resulting distances (e.g. same number as elements in the plurality of embeddings) may be sorted and the element with the smallest distance or the k elements with the k smallest distances may be output.

For example, the first stage (textual) model 230 has been trained to predict one or more of the coarse-grained search terms above. The user may input the query text 201 and may choose the respective field (e.g. catalytic activity, pathway or another) from a drop-down list or using a query language. The input query may use a controlled vocabulary in line with the coarse-grained search terms. Alternatively, the user may input the query text 201 and machine intelligence 210 may determine the respective field automatically. The respective search field may determine which textual model 230 to be used for transforming the query text into an embedding 260. The image embeddings may be transformed into their respective embeddings with a suitable visual model 220 (e.g. CNN), which was pre-trained using the embeddings of a respective textual model as described below, for example.

More details and aspects of the system 200 are mentioned in conjunction with the proposed concept and/or the one or more examples described above or below (e.g. FIGS. 1, 3-7). The system 200 may comprise one or more additional optional features corresponding to one or more aspects of the proposed concept and/or of one or more examples described above or below.

FIG. 3 shows a schematic illustration of a system 300 for processing biology-related data according to an embodiment. A user may start a query using text 201 (e.g. biology-related language-based search data) as in a protein sequence, nucleotide sequence or natural language, coarse-grained search terms or images. Optionally, a pre-classification of the query 201 using a suitable classifier 210 (e.g. a neural network, a statistical machine learning algorithm depending on input type) may be performed. The pre-classification can be skipped 315 in some embodiments. The results of the pre-classification may be used to select a suitable model 230 which can transform the user query 201 into its related semantic embedding 260 by a pre-trained model 230 which serves as a feature extractor.

User inputs and images coming from a data source 240 are connected and processed in this semantic embedding space. The data source 240 can be a private or public data repository or an imaging device such as a microscope. The data may be of type images, text, coarse-grained search terms or instrument specific data recorded by the data source. For example, a visual model 220 (e.g. CNN) may be included, which was trained on the semantic embeddings of a textual model, which was trained on a large body of protein sequences (e.g. protein sequence database), nucleotide sequences (e.g. nucleotide sequence database), scientific publications (e.g. database of biology-related publications) or other texts describing the role and biological function of the object of interest, such as blog posts, home pages of research groups, online articles, discussion forums or social media posts. The visual model 220 may have been pre-trained to predict these semantic embeddings during training. Both, the visual model 220 and the input feature extractor 230 (e.g. textual model) are trained on the same embedding space, for example. In another approach, the visual model 220 and the pretrained model 230 could be identical (e.g. if the search input is image based). The query 201 is then transformed into its respective embedding 260 using a forward pass through the input feature extractor 230. The data from the data source 240 which is either a database or part of a running experiment in a microscope may be transformed into its respective embeddings 250 via a forward pass through a pre-trained model 220 (visual model). For example, for performance reasons this procedure could be done prior to the user query and the semantic embeddings stored in a suitable database 255, or, for example, along with the image data. The database 240 and the database 255 may be identical or the same, but they could be different databases as well. However, for single or small numbers of images as in a running experiment the forward pass of the images can be done on-the-fly, thus bypassing 257 the intermediate storage 255 of the visual embeddings. The two kinds of generated embeddings, one embedding for the query 260 and the embeddings for the data source 250 can now be compared 270 in embedding space (e.g. their relative distances can be computed). Different distance metrics can be used for this comparison, such as Euclidean distance or Earth mover's distance. Other distance metrics may be used as well. For example, distance metrics used in clustering might work.

The system 300 may determine the closest embeddings 280, may look-up the respective data (e.g. images) in the repository 240 or running experiment and may return them 381. The last step can result in different downstream process steps depending on the exact purpose of the embodiment. In some cases, it may be necessary to feed by data 383, such as coordinates of the discovered object in terms of sample and stage coordinates, to the image source (e.g. microscope) which can change the course of the running experiment. In some embodiments the respective data can be output to the user 385 who may decide to adjust the running experiment or process the data further. Other embodiments may archive the respective data in a database 387 for future searches. Alternatively, the respective data, still in semantic embedding space, may be converted back to any of the input data types and may be used to query public databases 389 to retrieve scientific publications, social media entries or blog posts 390, images of that same biomolecule 393 or biological sequences as identified through a sequence alignment 395. All of the found information can be returned to the user 385 and or written to a database 387 as functional annotations of the images recorded in the currently running experiment or the repository, the retrieved data originated from.

FIG. 3 may show an example of a text-to-image search using text query. In one embodiment, the image repository 240 can represent a public or private database, in another embodiment it can represent the storage medium of a microscope during a running experiment.

More details and aspects of the system 300 are mentioned in conjunction with the proposed concept and/or the one or more examples described above or below (e.g. FIGS. 1-2 and 4-7). The system 300 may comprise one or more additional optional features corresponding to one or more aspects of the proposed concept and/or of one or more examples described above or below.

Figure 4:
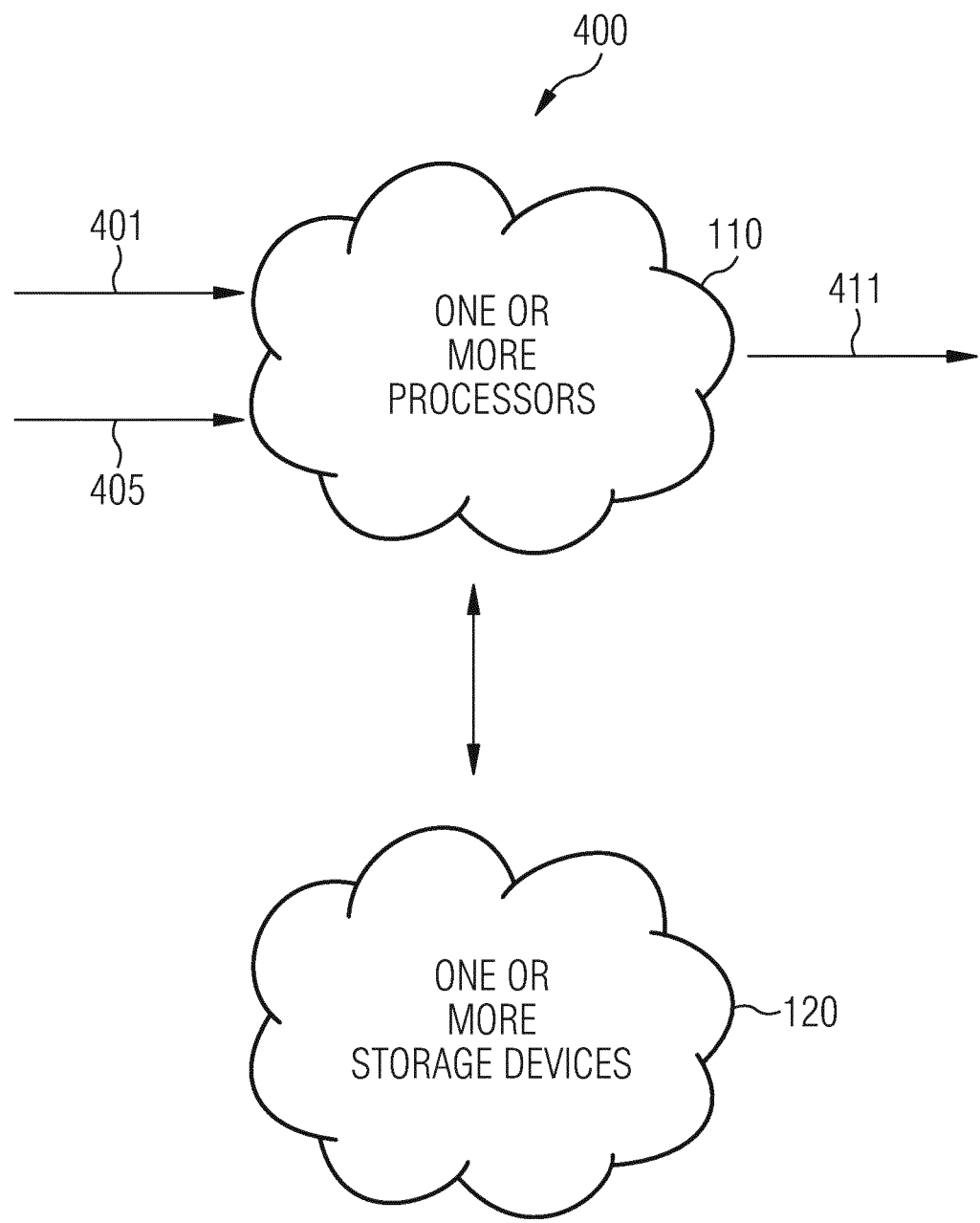
FIG. 4 is a schematic illustration of a system for controlling a microscope.

FIG. 4 shows a schematic illustration of a system 400 for controlling a microscope according to an embodiment. The system 400 comprises one or more processors 110 and one or more storage devices 120. The system 400 is configured to receive language-based search data 401 and configured to generate a first high-dimensional representation of the language-based search data 401 by a trained language recognition machine-learning algorithm executed by the one or more processors 110. The first high-dimensional representation comprises at least 3 entries each having a different value (or at least 20 entries, at least 50 entries or at least 100 entries having values different from each other). Further, the system 400 is configured to obtain a plurality of second high-dimensional representations 405 of a plurality of image-based input data sets and configured to select a second high-dimensional representation 405 from the plurality of second high-dimensional representations based on a comparison of the first high-dimensional representation with each second high-dimensional representation 405 of the plurality of second high-dimensional representations performed by the one or more processors 110. Additionally, the system 400 is configured to provide a control signal 411 for controlling an operation of a microscope based on the selected second high-dimensional representation 405.

The language-based search data 401 may be a textual input and may describe a feature of a specimen, which is to be found or analyzed. The specimen to be analyzed may be a biological specimen, an integrated circuit or any other specimen, which can be imaged by a microscope. For example, if the specimen is a biological specimen, the language-based search data 401 may be a biology-related language-based search data, for example a nucleotide sequence, a protein sequence, a description of a biological molecule or biological structure, a description of a behavior of a biological molecule or biological structure, and/or a description of a biological function or a biological activity. The textual input may be natural language, which is descriptive of the biological molecule (e.g. polysaccharide, poly/oligonucleotide, protein or lipid) or its behavior in the context of the experiment or data set. For example, the language-based search data 401 may be a nucleotide sequence, a protein sequence or a coarse-grained search term of a group of biological terms. For example, if the specimen is an integrated circuit, the language-based search data 401 may be a description, definition or representation of a sub-circuit (e.g. memory cell, converter cell, ESD protection circuit), a circuit element (e.g. transistor, capacitor or coil) or a structural element (e.g. gate, via, pad or spacer).

The plurality of second high-dimensional representations 405 may be obtained from a database or may be generated by a visual recognition machine-learning algorithm. For example, the system 400 may be configured to generate the plurality of second high-dimensional representations 405 of the plurality of image-based input data sets by a visual recognition machine-learning algorithm executed by the one or more processors 110.

A microscope may be configured to take a plurality of images of a specimen. The plurality of image-based input data sets may represent the plurality of images of the specimen. The plurality of image-based input data sets may be image data of images taken by the microscope from a specimen. For example, a plurality of images may be taken from specimen at different positions to cover to whole specimen or a region of interest of the specimen, which is too large to be taken by a single image at a desired magnification. The image data of each image of the plurality of images may represent one image-based input data set of the plurality of image-based input data sets. The system 400 may be configured to store the positions, the images were taken from. The positions may be stored together with the corresponding images or together with the corresponding second high-dimensional representations 405. The system 400 may comprise the microscope or the microscope may be connected to the system 400 or may comprise the system 400.

The system 400 may select a second high-dimensional representation of the plurality of second high-dimensional representations, which fulfills a selection criterion (e.g. second high-dimensional representation, which is closest to the first high-dimensional representation). The comparison of the first high-dimensional representation with each second high-dimensional representation of the plurality of second high-dimensional representations may provide one or more second high-dimensional representations closest to the first high-dimensional representation. The system 400 may be configured to select one or more second high-dimensional representations of the plurality of second high-dimensional representations closest to the first high-dimensional representation based on the comparison.

The system 400 may be configured to determine a microscope target position based on the selected second high-dimensional representation. The microscope target position may be the position, the image was taken from, which corresponds to the selected second high-dimensional representation. For example, the microscope target position may be the position stored together with the selected second high-dimensional representation or together with the image, which corresponds to the selected second high-dimensional representation. The microscope target position may be the position at which an image was taken, which was represented by the image-based input data, which corresponds to the selected second high-dimensional representation.

The system 400 may be configured to provide the control signal for controlling an operation of a microscope based on the determined microscope target position. The control signal 411 may be an electrical signal provided to the microscope to control a movement, a magnification, a light source selection, a filter selection and/or another microscope functionality. For example, the control signal 411 may be configured to trigger the microscope to drive to the microscope target position. For example, the optics and/or the specimen table of the microscope may be moved to the microscope target position in response to the control signal 411. In this way, further images can be taken from the specimen at the position, which was the result of the search. For example, images with higher magnification, different light source and/or different filter could be taken of a region of interest. For example, the language-based search data 405 may represent the search for cell nuclei in a large biological specimen and the system 400 may provide a control signal 411 for driving the microscope to a position of a cell nucleus. If several cell nuclei may be found, the system 400 may be configured to provide the control signal 411 so that the microscope is driven to the different positions one after the other in order to take more images at these positions.

More details and aspects of the system 400 are mentioned in conjunction with the proposed concept and/or the one or more examples described above or below (e.g. FIGS. 1-3 and 5-7). The system 400 may comprise one or more additional optional features corresponding to one or more aspects of the proposed concept and/or of one or more examples described above or below.

The system described in conjunction with one of the FIGS. 1-4 may comprise or may be a computer device (e.g. personal computer, laptop, tablet computer or mobile phone) with the one or more processors and one or more storage devices located in the computer device or the system may be a distributed computing system (e.g. cloud computing system with the one or more processors and one or more storage devices distributed at various locations, for example, at a local client and one or more remote server farms and/or data centers). The system may comprise a data processing system that includes a system bus to couple the various components of the system. The system bus may provide communication links among the various components of the system and may be implemented as a single bus, as a combination of busses, or in any other suitable manner. An electronic assembly may be coupled to the system bus. The electronic assembly may include any circuit or combination of circuits. In one embodiment, the electronic assembly includes a processor which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA) of the microscope or a microscope component (e.g. camera) or any other type of processor or processing circuit. Other types of circuits that may be included in electronic assembly may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The system includes one or more storage devices, which in turn may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The system may also include a display device, one or more speakers, and a keyboard and/or controller, which can include a mouse, trackball, touch screen, voice-recognition device, or any other device that permits a system user to input information into and receive information from the system.

Additionally, the system may comprise a microscope connected to a computer device or a distributed computing system. The microscope may be configured to generate the biology-related image-based input data sets by taking images from one or more specimens.

The microscope may be a light microscope (e.g. diffraction limited or sub-diffraction limit microscope as, for example, a super-resolution microscope or nanoscope). The microscope may be a stand-alone microscope or a microscope system with attached components (e.g. confocal scanners, additional cameras, lasers, climate chambers, automated loading mechanisms, liquid handling systems, optical components attached, like additional multiphoton light paths, optical tweezers and more). Other image sources may be used as well, if they can take images of objects which are related to biological sequences (e.g. proteins, nucleic acids, lipids) or other specimens, for example. For example, a microscope according to an embodiment described above or below may enable deep discovery microscopy.

More details and aspects of the system are mentioned in conjunction with the proposed concept and/or the one or more examples described above or below (e.g. FIGS. 1-7). The system may comprise one or more additional optional features corresponding to one or more aspects of the proposed concept and/or of one or more examples described above or below.

Figure 5:
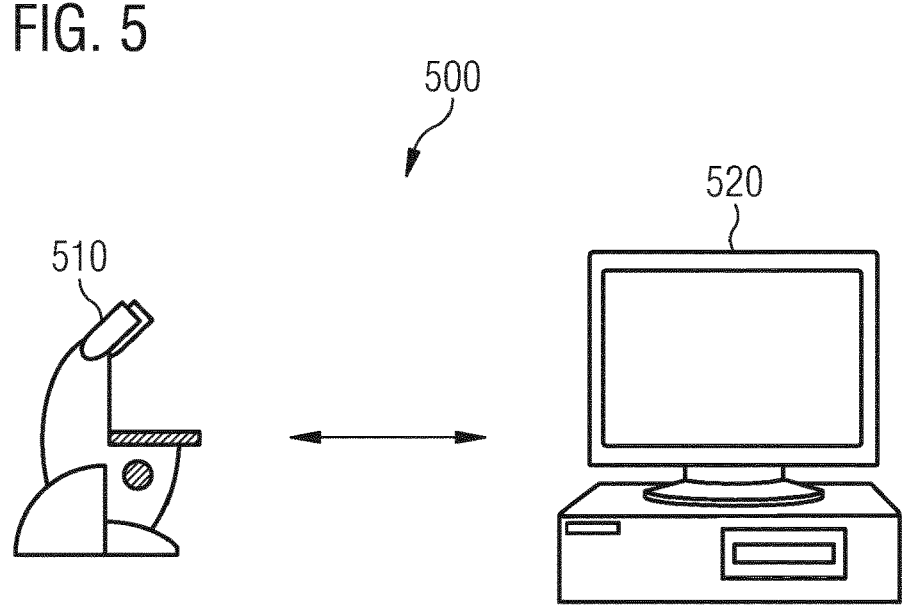
FIG. 5 is a schematic illustration of a system for processing data.

Some embodiments relate to a microscope comprising a system as described in conjunction with one or more of the FIGS. 1-4. Alternatively, a microscope may be part of or connected to a system as described in conjunction with one or more of the FIGS. 1-4. FIG. 5 shows a schematic illustration of a system 500 for processing data according to an embodiment. A microscope 510 configured to take images of one or more specimens (e.g. biological specimens or integrated circuits) is connected to a computer device 520 (e.g. personal computer, laptop, tablet computer or mobile phone) configured to process data. The microscope 510 and the computer device 520 may be implemented as described in conjunction with one or more of the FIGS. 1-4.

Figure 6:
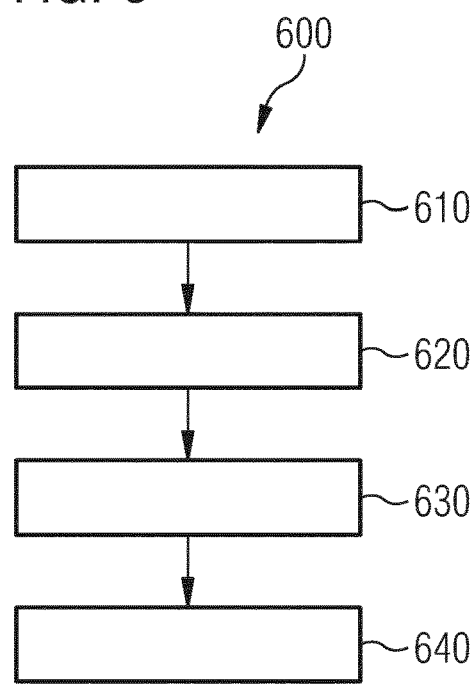
FIG. 6 is a flow chart of a method for processing biology-related data.

FIG. 6 shows a flow chart of a method for processing biology-related language-based search data according to an embodiment. The method 600 comprises receiving 610 biology-related language-based search data and generating 620 a first high-dimensional representation of the biology-related language-based search data by a trained language recognition machine-learning algorithm. The first high-dimensional representation comprises at least 3 entries each having a different value. Further, the method 600 comprises obtaining 630 a plurality of second high-dimensional representations of a plurality of biology-related image-based input data sets or a plurality of biology-related language-based input data sets. Additionally, the method comprises comparing 640 the first high-dimensional representation with each second high-dimensional representation of the plurality of second high-dimensional representations.

By using a language recognition machine-learning algorithm textual biological search terms can be mapped to a high-dimensional representation. By allowing the high-dimensional representation to have entries with various different values (in contrast to one hot encoded representations), semantically similar biological search terms can be mapped to similar high-dimensional representations. By obtaining high-dimensional representations of a plurality of biology-related image-based input data sets or of a plurality of biology-related language-based input data sets, high-dimensional representations can be found equal or similar to the high-dimensional representation of the search term. In this way, it may be enabled to find images or text corresponding to the search term. In this way, the trained language recognition machine-learning algorithm may enable a search of biology-related images among a plurality of biological images (e.g. database of biological images) or a search of biology-related texts among a plurality of biology related texts (e.g. scientific paper collection or library) based on a language-based search input. A search within an already existing database or images generated by a running experiment (e.g. images taken by a microscope of one or more biological specimens) may be enabled, even if the images were not labeled or tagged before.

More details and aspects of method 600 are mentioned in conjunction with the proposed concept and/or the one or more examples described above or below (e.g. FIGS. 1-5). The method 600 may comprise one or more additional optional features corresponding to one or more aspects of the proposed concept and/or of one or more examples described above or below.

Figure 7:
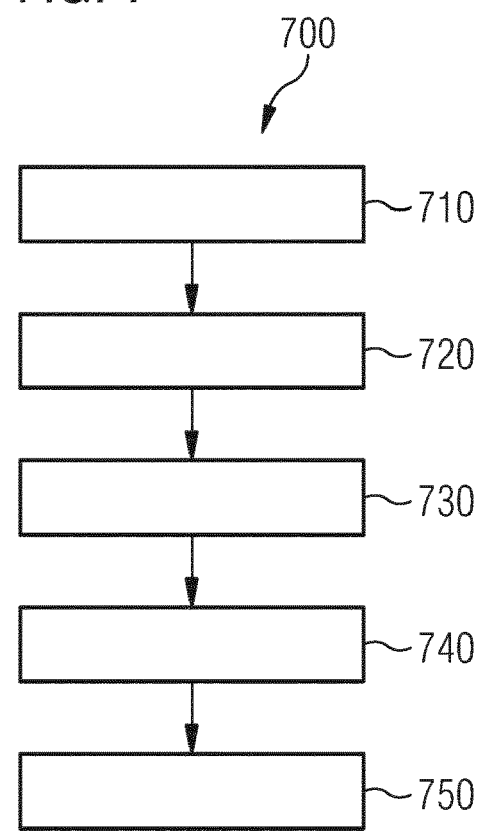
FIG. 7 is a flow chart of a method for controlling a microscope.

FIG. 7 shows a flow chart of a method for controlling a microscope according to an embodiment. The method 700 comprises receiving 710 language-based search data and generating 720 a first high-dimensional representation of the language-based search data by a trained language recognition machine-learning algorithm. The first high-dimensional representation comprises at least 3 entries each having a different value. Further, the method 700 comprises obtaining 730 a plurality of second high-dimensional representations of a plurality of image-based input data sets and selecting 740 a second high-dimensional representation from the plurality of second high-dimensional representations based on a comparison of the first high-dimensional representation with each second high-dimensional representation of the plurality of second high-dimensional representations. Additionally, the method 700 comprises controlling 750 an operation of a microscope based on the selected second high-dimensional representation.

By using a language recognition machine-learning algorithm textual search terms can be mapped to a high-dimensional representation. By allowing the high-dimensional representation to have entries with various different values (in contrast to one hot encoded representations), semantically similar search terms can be mapped to similar high-dimensional representations. By obtaining high-dimensional representations of a plurality of image-based input data sets, high-dimensional representations can be found equal or similar to the high-dimensional representation of the search term. In this way, it may be enabled to find images corresponding to the search term. With this information, a microscope can be driven to the respective locations, the images were taken, in order to enable taking further images (e.g. with higher magnification, different light or filter) of the locations of interest. In this way, a specimen (e.g. biological specimen or integrated circuit) may be imaged at low magnification first to find locations corresponding to the search term and afterwards the locations of interest may be analyzed in more detail.

More details and aspects of method 700 are mentioned in conjunction with the proposed concept and/or the one or more examples described above or below (e.g. FIGS. 1-5). The method 700 may comprise one or more additional optional features corresponding to one or more aspects of the proposed concept and/or of one or more examples described above or below.

In the following, some examples of applications and/or implementation details for one or more of the embodiments described above (e.g. in conjunction with one or more of the FIGS. 1-7) are described.

According to an aspect, a text-to-image search functionality in databases or running microscopy experiments is proposed. The type of text-to-image search may be based on semantic embeddings of the query text created by a first stage textual model. A second stage image model may relate these semantic embeddings to images thus connecting the image domain to the text domain. Relevance of the hits may be scored according to a distance metric in the semantic embedding space. This may allow retrieval not only of exact matches, but also retrieval of similar images with related semantics. In the context of biology related semantics may mean similar biological function.

Biology in general and microscopy in particular may generate vast amounts of data, which often gets poorly annotated or not annotated at all. For example, it may only become apparent in retrospect which annotations might have been useful or new biological discoveries are made not known at the time of the experiment. The emphasis may be on image data, but the proposed concept might not necessarily be restricted to image data. Images may go beyond 2D pixel maps, but rather encompass multidimensional image tensors with three spatial dimensions, a time dimension and further dimensions related to physical properties of the fluorescence dyes used or to properties of the imaging system, for example. According to an aspect, such data may be made accessible by allowing semantic searching of large bodies of image data stored in a database or as part of a running experiment in a microscope. The experiment may be a single one-time experiment or part of a long-term experiment such as a screening campaign.

In the context of a running experiment, the proposed concept may help to automate searching biological structures, which are part of a specimen such as proteins expressed in single cells, organoids or tissues, but also more general structures such as organs or developmental states. In this way, an automation of a time-consuming step of finding the relevant parts within a specimen may be enabled.

For other concepts, querying images through text may rely on annotations made by a human expert. Each annotation may serve as a dimension to narrow down the search. However, such annotations are often not available or time-consuming to create. According to an aspect, distance metrics in semantic embedding space may be used. This approach might not only remove the strict necessity for human annotations but may also provide a measure for functional (e.g. biological) similarity between images.

In the context of a running microscopy experiment, the proposed concept may remove the time-consuming step of finding relevant structures in a microscope specimen. Instead of manually searching through the specimen, the user may input a search query and a proposed microscope may find the relevant objects in the specimen. This approach may also remove individual bias often brought about by manual searching.

In addition, using semantic embeddings may allow the logical or arithmetic combination of query elements. For example, a search for "clathrin" (which has a speckled appearance in the cytoplasm) and "nucleus" might show a lot of proteins in the nucleus which have a speckled appearance (but are not necessarily known interactors of clathrin). Conversely, a more narrow search for "ATP Synthase" and "Cytochrome c oxidase", two known interactors which are part of the oxidative phosphorylation pathway in the mitochondrium might yield more proteins related to oxidative phosphorylation as well as proteins located at the mitochondrium. Thus, both, searches for known biological interactors as well as possible (and even impossible, i.e. unlikely) new interactors can be discovered.

According to an aspect, a text-to-image search may be enabled. Image databases currently in use for search and retrieval of microscopic images may use classical tagging and annotations to make images searchable. The proposed concept may make images searchable where there are no good annotations available. For example, one may be able to search for biological function, which has not been explicitly annotated. The annotation otherwise would require time and work from experts, which may be saved here.

For example, one can get approximate hits, which are semantically close, but not identical to the search term. This property, also known as zero-shot learning (e.g. identifying classes, which have not been contained in the training set) might not be available when using other techniques.

Further, logical operations on query terms may result in semantic arithmetic. For example, one can combine search terms to get the sematic combination of them in an image, such as searching for "clathrin" and "nucleus" could retrieve nuclear speckes. This property may be only available, if semantics are represented as computable entities. According to an aspect, the semantics may be represented as latent vectors.

The proposed concept may be implemented in an imaging system (such as a microscope). In this way, related objects with the same (or a similar) biological function may be identified in a specimen based on a textual search using biological sequences, natural language or coarse-grained search terms, for example.

The type of text-to-image search according to an aspect may be based on creating semantic embeddings by a first stage textual model from the query text and a second stage image model relating semantic embeddings to images, thus connecting the image domain to the text domain. The relevance of the hits may be scored according to a distance metric in the semantic embedding space. The first and second stage model may be trained as described below, but can be trained in a different way also.

Text-to-image search may make images which have not been annotated with suitable search terms searchable by text queries. So, manual work by experts may be saved and bias may be removed. An application field may be the search of existing image databases, but also running experiments in a microscope or bioimaging device. Biology in particular may suffer from producing large amounts of data in the form of biological sequences, descriptive text and images on the on hand, but often not having standardized or any annotations with the data (e.g. the latter mainly applies to images). The feature space of biological images compared to photographs may be limited, making it hard for traditional approaches to tell them apart. According to an aspect, the power of deep learning-based image models (e.g. CNNs or CapsNets) for image cognition may be combined with the functional information contained in biological sequences or descriptive text. The sequences and text thus may serve as proxy for biological functions.

Moreover, it may be enabled to get approximate hits, which are semantically related to the search term, but not identical with it. This may help with retrieving related images from a database or a specimen the user didn't know was there. In light of increasing data volume and availability of previous experiments, this may help to turn an existing image repository into a data asset, which is useful not only to the researchers who conducted the experiment. Another application may be the search for combined search terms. Combination on the user level may look like concatenation or entering multiple search terms. Internally, those terms may be converted into semantic embeddings, which are vectors that can undergo arithmetic. For example, new relationships within the data repository or running experiment can be discovered. In comparison to annotations by experts, the latter may only be able to annotate what they know about or anticipate, but new discoveries may lead to new research questions. Text-to-image search according to the proposed concept may thus allow to ask new questions to existing data so that its value may be increased. Applications of the proposed text-to-image search may be basic biological research, helping to find relevant data and reduce experimental recording time, and/or hit validation and toxicology assays in drug discovery, for example.

A trained language recognition machine-learning algorithm and/or a trained visual recognition machine-learning algorithm may be obtained by a training described in the following. A system for training machine-learning algorithms for processing biology-related data may comprise one or more processors and one or more storage devices. The system may be configured to receive biology-related language-based input training data. Additionally, the system may be configured to generate a first high-dimensional representation of the biology-related language-based input training data by a language recognition machine-learning algorithm executed by the one or more processors. The first high-dimensional representation comprises at least three entries each having a different value. Further, the system may be configured to generate biology-related language-based output training data based on the first high-dimensional representation by the language recognition machine-learning algorithm executed by the one or more processors. In addition, the system may be configured to adjust the language recognition machine-learning algorithm based on a comparison of the biology-related language-based input training data and the biology-related language-based output training data. Additionally, the system may be configured to receive biology-related image-based input training data associated with the biology-related language-based input training data. Further, the system may be configured to generate a second high-dimensional representation of the biology-related image-based input training data by a visual recognition machine-learning algorithm executed by the one or more processors. The second high-dimensional representation comprises at least three entries each having a different value. Further, the system may be configured to adjust the visual recognition machine-learning algorithm based on a comparison of the first high-dimensional representation and the second high-dimensional representation.

The biology-related language-based input training data may be a textual input being related to a biological structure, a biological function, a biological behavior or a biological activity. For example, the biology-related language-based input training data may be a nucleotide sequence, a protein sequence, a description of a biological molecule or biological structure, a description of a behavior of a biological molecule or biological structure, and/or a description of a biological function or a biological activity. The biology-related language-based input training data may be a first biology-related language-based input training data set (e.g. sequence of input characters, for example, a nucleotide sequence or a protein sequence) of a training group. The training group may comprise a plurality of biology-related language-based input training data sets.

The biology-related language-based output training data may be of the same type as the biology-related language-based input training data including optionally a prediction of a next element. For example, the biology-related language-based input training data may be a biological sequence (e.g. a nucleotide sequence or a protein sequence) and the biology-related language-based output training data may be a biological sequence (e.g. a nucleotide sequence or a protein sequence) as well. The language recognition machine-learning algorithm may be trained so that the biology-related language-based output training data is equal to the biology-related language-based input training data including optionally a prediction of a next element of the biological sequence. In another example, the biology-related language-based input training data may be a biological class of a coarse-grained search term and the biology-related language-based output training data may be a biological class of the coarse-grained search term as well.

The biology-related image-based input training data may be image training data (e.g. pixel data of a training image) of an image of a biological structure comprising a nucleotide or a nucleotide sequence, a biological structure comprising a protein or a protein sequence, a biological molecule, a biological tissue, a biological structure with a specific behavior, and/or a biological structure with a specific biological function or a specific biological activity. The biology-related image-based input training data may be a first biology-related image-based input training data set of a training group. The training group may comprise a plurality of biology-related image-based input training data sets.

The biology-related language-based input training data may be a biology-related language-based input training data set (e.g. sequence of input characters, for example, a nucleotide sequence or a protein sequence) of a training group. The training group may comprise a plurality of biology-related language-based input training data sets. The system may repeat generating a first high-dimensional representation for each of a plurality of biology-related language-based input training data sets of a training group. Further, the system may generate biology-related language-based output training data for each generated first high-dimensional representation. The system may adjust the language recognition machine-learning algorithm based on each comparison of biology-related language-based input training data of the plurality of biology-related language-based input training data sets of the training group with the corresponding biology-related language-based output training data. In other words, the system may be configured to repeat generating a first high-dimensional representation, generating biology-related language-based output training data, and adjusting the language recognition machine-learning algorithm for each biology-related language-based input training data of a training group of biology-related language-based input training data sets. The training group may comprise enough biology-related language-based input training data sets so that a training target (e.g. variation of an output of a loss function below a threshold) can be fulfilled.

The plurality of all first high-dimensional representations generated during training of the language recognition machine-learning algorithm may be called latent space or semantic space.

The system may repeat generating a second high-dimensional representation for each of a plurality of biology-related image-based input training data sets of a training group. Further, the system may adjust the visual recognition machine-learning algorithm based on each comparison of a first high-dimensional representation with the corresponding second high-dimensional representation. In other words, the system may repeat generating a second high-dimensional representation and adjusting the visual recognition machine-learning algorithm for each biology-related image-based input training data of a training group of biology-related image-based input training data sets. The training group may comprise enough biology-related image-based input training data sets so that a training target (e.g. variation of an output of a loss function below a threshold) can be fulfilled.

For example, the system 100 uses a combination of a language recognition machine-learning algorithm and a visual recognition machine-learning algorithm (e.g. also called visual-semantic model). The language recognition machine-learning algorithm and/or the visual recognition machine-learning algorithm may be deep learning algorithms and/or artificial intelligence algorithms.

The training may converge fast and/or may provide a well-trained algorithm for biology-related data by using the cross entropy loss function for training the language recognition machine-learning algorithm, although other loss functions could be used as well.

The visual recognition machine-learning algorithm may be trained by adjusting parameters of the visual recognition machine-learning algorithm based on the comparison of a high dimensional representation generated by the language recognition machine-learning algorithm with a high dimensional representation generated by the visual recognition machine-learning algorithm of corresponding input training data. For example, network weights of a visual recognition neural network may be adjusted based on the comparison. The adjustment of the parameters (e.g. network weights) of the visual recognition machine-learning algorithm may be done under consideration of a loss function. For example, the comparison of the first high-dimensional representation and the second high-dimensional representation for the adjustment of the visual recognition machine-learning algorithm may be based on a cosine similarity loss function. The training may converge fast and/or may provide a well-trained algorithm for biology-related data by using the cosine similarity loss function for training the visual recognition machine-learning algorithm, although other loss functions could be used as well.

For example, the visual model may learn how to represent an image in the semantic embedding space (e.g. as a vector). So, a measure for the distance of two vectors may be used, which may represent the prediction A (the second high-dimensional representation) and the ground-truth B (the first high-dimensional representation). For example, a measure is the cosine similarity as defined in $$\text{similarity} = \cos(\theta) = \frac{A \cdot B}{\|A\|\|B\|}$$

with the dot product of the prediction A and ground-truth B divided by the dot product of their respective magnitudes (e.g. as in L2-Norm or Euclidian norm).

More details with respect to non-training specific aspects of the system for training machine-learning algorithms are mentioned in conjunction with the proposed concept and/or the one or more examples described above or below (e.g. FIGS. 1-7).

Embodiments may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and/or training sequences (e.g. words or sentences) and associated training content information (e.g. labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e. each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm, e.g. a classification algorithm, a regression algorithm or a similarity learning algorithm. Classification algorithms may be used when the outputs are restricted to a limited set of values, i.e. the input is classified to one of the limited set of values. Regression algorithms may be used when the outputs may have any numerical value (within a range). Similarity learning algorithms may be similar to both classification and regression algorithms, but are based on learning from examples using a similarity function that measures how similar or related two objects are. Apart from supervised or semi-supervised learning, unsupervised learning may be used to train the machine-learning model. In unsupervised learning, (only) input data might be supplied, and an unsupervised learning algorithm may be used to find structure in the input data, e.g. by grouping or clustering the input data, finding commonalities in the data. Clustering is the assignment of input data comprising a plurality of input values into subsets (clusters) so that input values within the same cluster are similar according to one or more (predefined) similarity criteria, while being dissimilar to input values that are included in other clusters.

Reinforcement learning is a third group of machine-learning algorithms. In other words, reinforcement learning may be used to train the machine-learning model. In reinforcement learning, one or more software actors (called "software agents") are trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards).

Furthermore, some techniques may be applied to some of the machine-learning algorithms. For example, feature learning may be used. In other words, the machine-learning model may at least partially be trained using feature learning, and/or the machine-learning algorithm may comprise a feature learning component. Feature learning algorithms, which may be called representation learning algorithms, may preserve the information in their input, but also transform it in a way that makes it useful, often as a pre-processing step before performing classification or predictions. Feature learning may be based on principal components analysis or cluster analysis, for example.

In some examples, anomaly detection (i.e. outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g. a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g. be used to store, manipulate or apply the knowledge.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge, e.g. based on the training performed by the machine-learning algorithm. In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of the sum of its inputs. The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input.

Alternatively, the machine-learning model may be a support vector machine, a random forest model or a gradient boosting model. Support vector machines (i.e. support vector networks) are supervised learning models with associated learning algorithms that may be used to analyze data, e.g. in classification or regression analysis. Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a nontransitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier. For example, the computer program may be stored on a non-transitory storage medium. Some embodiments relate to a non-transitory storage medium including machine readable instructions, when executed, to implement a method according to the proposed concept or one or more examples described above.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS 100 system for processing biology-related data
101 biology-related language-based search data
105 second high-dimensional representation
110 one or more processors
120 one or more storage devices
200 system for processing biology-related data
201 query, search query, biology-related language-based search data
210 text model, classifier
220 trained visual recognition machine-learning algorithm, visual model
230 trained language recognition machine-learning algorithm, textual model, language model
240 database
250 embeddings, plurality of second high-dimensional representations
255 database, intermediate storage
257 bypass
260 embedding, first high-dimensional representation
270 comparison in embedding space
280 closest embedding
290 respective image
300 system for processing biology-related data
315 skipped pre-classification
381 return image corresponding to closest embedding
383 feed by of data to the image source
385 user
387 database
389 public database
390 scientific publications, social media entries or blog posts
393 image of biomolecule 395 biological sequence
400 system for controlling a microscope
401 language-based search data
405 second high-dimensional representation
411 control signal
500 system for processing data
510 microscope
520 computer device
600 method for processing biology-related language-based search data
610 receiving biology-related language-based search data
620 generating a first high-dimensional representation
630 obtaining a plurality of second high-dimensional representations
640 comparing the first high-dimensional representation with each second high-dimensional representation
700 method for controlling a microscope
710 receiving language-based search data
720 generating a first high-dimensional representation
730 obtaining a plurality of second high-dimensional representations
740 selecting a second high-dimensional representation
750 controlling an operation of a microscope

The invention claimed is:

1. A system comprising one or more processors and one or more storage devices, wherein the system is configured to:
receive biology-related language-based search data, wherein the biology-related language-based search data is at least one of a nucleotide sequence, a protein sequence, a description of a biological molecule or biological structure, a description of a behavior of a biological molecule or biological structure, or a description of a biological function or a biological activity;
generate a first high-dimensional representation of the biology-related language-based search data by a trained language recognition machine-learning algorithm executed by the one or more processors, wherein the first high-dimensional representation comprises at least 3 entries each having a different value,
wherein the system is configured to select the trained language recognition machine-learning algorithm from a plurality of trained language recognition machine-learning algorithms based on the biology-related language-based search data;
obtain a plurality of second high-dimensional representations of a plurality of biology-related image-based input data sets or of a plurality of biology-related language-based input data sets;
compare the first high-dimensional representation with each second high-dimensional representation of the plurality of second high-dimensional representations; and
select a second high-dimensional representation of the plurality of second high-dimensional representations closest to the first high-dimensional representation based on the comparison.

2. The system of claim 1, wherein the values of one or more entries of the first high-dimensional representation are proportional to a likelihood of a presence of a specific biological function or a specific biological activity.

3. The system of claim 1, wherein the values of one or more entries of the second high-dimensional representations are proportional to a likelihood of a presence of a specific biological function or a specific biological activity.

4. The system of claim 1, further comprising a microscope configured to obtain the plurality of biology-related image-based input data sets by taking images of a biological specimen.

5. The system of claim 1, wherein the system is configured to output at least one of the closest second high-dimensional representation, the biology-related image-based input data set of the plurality of biology-related image-based input data sets, which corresponds to the closest second high-dimensional representation, or the biology-related language-based input data set of the plurality of biology-related language-based input data sets, which corresponds to the closest second high-dimensional representation.

6. The system of claim 1, wherein the comparison of the first high-dimensional representation with each second high-dimensional representation of the plurality of second high-dimensional representations is based on an Euclidean distance function or an earth mover's distance function.

7. The system of claim 1, wherein the first high-dimensional representation and the second high-dimensional representations are numerical representations.

8. The system of claim 1, wherein the first high-dimensional representation and the second high-dimensional representations comprise each more than 100 dimensions.

9. The system of claim 1, wherein the first high-dimensional representation is a first vector and the second high-dimensional representations are second vectors.

10. The system of claim 1, wherein more than 50% of values of the entries of the first high-dimensional representation and more than 50% of values of the entries of the second high-dimensional representations are unequal 0.

11. The system of claim 1, wherein the values of more than 5 entries of the first high-dimensional representation are larger than 10% of a largest absolute value of the entries of the first high-dimensional representation and the values of more than 5 entries of each second high-dimensional representation of the plurality of second high-dimensional representations are larger than 10% of a respective largest absolute value of the entries of the second high-dimensional representations.

12. The system of claim 1, wherein the biology-related language-based search data comprises a length of more than 20 characters.

13. The system of claim 1, wherein the trained language recognition machine-learning algorithm comprises a trained language recognition neural network.

14. The system of claim 13, wherein the trained language recognition neural network comprises more than 30 layers.

15. The system of claim 13, wherein the trained language recognition neural network is a recurrent neural network.

16. The system of claim 13, wherein the trained language recognition neural network is a long short-term memory network.

17. The system of claim 1, wherein the system is configured to generate:
the second high-dimensional representations of the plurality of second high-dimensional representations of the plurality of biology-related image-based input data sets using a trained visual recognition machine-learning algorithm; or
the second high-dimensional representations of the plurality of second high-dimensional representations of the plurality of biology-related language-based input data sets using a trained language recognition machine-learning algorithm, wherein each second high-dimensional representation of the plurality of second high-dimensional representations comprises at least 3 entries each having a different value.

18. The system of claims 17, wherein the trained visual recognition machine-learning algorithm comprises a trained visual recognition neural network.

19. The system of claim 18, wherein the trained visual recognition neural network comprises more than 30 layers.

20. The system of claim 18, wherein the trained visual recognition neural network is a convolutional neural network or a capsule network.

21. The system of claim 18, wherein the trained visual recognition neural network comprises a plurality of convolution layers and a plurality of pooling layers.

22. The system of claim 18, wherein the trained visual recognition neural network uses a rectified linear unit activation function.

23. The system of claim 17, wherein the trained visual recognition machine-learning algorithm or the trained language recognition machine-learning algorithm for generating the plurality of second high-dimensional representations and the trained language recognition machine-learning algorithm for generating the first high-dimensional representation are all trained on an identical embedding space.

24. The system of claim 1, wherein the system is configured to:
receive second biology-related language-based search data and information on a logical operator;
generate a first high-dimensional representation of the second biology-related language-based search data by the trained language recognition machine-learning algorithm executed by the one or more processors;
determine a combined high-dimensional representation based on a combination of the first high-dimensional representation of the first biology-related language-based search data and the first high-dimensional representation of the second biology-related language-based search data according to the logical operator; and
compare the combined high-dimensional representation to each second high-dimensional representation of the plurality of second high-dimensional representations.

25. The system of claim 24, wherein the logical operator is an AND-operator and the combined high-dimensional representation is determined by adding the first high-dimensional representation of the first biology-related language-based search data and the first high-dimensional representation of the second biology-related language-based search data.

26. A microscope comprising a system of claim 1.

27. A system comprising one or more processors and one or more storage devices, wherein the system is configured to:
receive language-based search data;
generate a first high-dimensional representation of the language-based search data by a trained language recognition machine-learning algorithm executed by the one or more processors, wherein the first high-dimensional representation comprises at least 3 entries each having a different value,
wherein the system is configured to select the trained language recognition machine-learning algorithm from a plurality of trained language recognition machine-learning algorithms based on the language-based search data;
obtain a plurality of second high-dimensional representations of a plurality of image-based input data sets;
select a second high-dimensional representation from the plurality of second high-dimensional representations based on a comparison of the first high-dimensional representation with each second high-dimensional representation of the plurality of second high-dimensional representations;
provide a control signal for controlling an operation of a microscope based on the selected second high-dimensional representation.

28. The system of claim 27, wherein the system is configured to determine a microscope target position based on the selected second high-dimensional representation, wherein the microscope target position is a position at which an image was taken, which was represented by the image-based input data, which corresponds to the selected second high-dimensional representation, wherein the control signal is configured to trigger the microscope to drive to the microscope target position.

29. The system of claim 27, wherein the system is configured to generate the plurality of second high-dimensional representations of the plurality of image-based input data sets by a visual recognition machine-learning algorithm executed by the one or more processors.

30. The system of claim 27, wherein the system is configured to select a second high-dimensional representation of the plurality of second high-dimensional representations closest to the first high-dimensional representation based on the comparison.

31. The system of claim 27, further comprising the microscope configured to take a plurality of images of a specimen, wherein the plurality of image-based input data sets represents the plurality of images of the specimen.

32. A method for processing biology-related language-based search data, the method comprising:
receiving biology-related language-based search data, wherein the biology-related language-based search data is at least one of a nucleotide sequence, a protein sequence, a description of a biological molecule or biological structure, a description of a behavior of a biological molecule or biological structure, or a description of a biological function or a biological activity;
generating a first high-dimensional representation of the biology-related language-based search data by a trained language recognition machine-learning algorithm, wherein the first high-dimensional representation comprises at least 3 entries each having a different value, wherein the trained language recognition machine-learning algorithm is selected from a plurality of trained language recognition machine-learning algorithms based on the biology-related language-based search data;
obtaining a plurality of second high-dimensional representations of a plurality of biology-related image-based input data sets or a plurality of biology-related language-based input data sets; and
comparing the first high-dimensional representation with each second high-dimensional representation of the plurality of second high-dimensional representations; and
selecting a second high-dimensional representation of the plurality of second high-dimensional representations closest to the first high-dimensional representation based on the comparison.

33. A method for controlling a microscope, the method comprising:
receiving language-based search data;

generating a first high-dimensional representation of the language-based search data by a trained language recognition machine-learning algorithm, wherein the first high-dimensional representation comprises at least 3 entries each having a different value,
 wherein the trained language recognition machine-learning algorithm is selected from a plurality of trained language recognition machine-learning algorithms based on the language-based search data;
obtaining a plurality of second high-dimensional representations of a plurality of image-based input data sets;
selecting a second high-dimensional representation from the plurality of second high-dimensional representations based on a comparison of the first high-dimensional representation with each second high-dimensional representation of the plurality of second high-dimensional representations; and
controlling an operation of a microscope based on the selected second high-dimensional representation.

* * * * *